United States Patent [19]

Nakanishi et al.

[11] Patent Number: 5,210,074
[45] Date of Patent: May 11, 1993

[54] METHOD FOR PREPARING A DRIED COMPOSITION OF INSULIN-LIKE GROWTH FACTOR I

[75] Inventors: Shigeo Nakanishi, Neyagawa; Iwao Yamanaka, Osaka, both of Japan

[73] Assignee: Fujisawa Pharmaceutical Co., Ltd., Osaka, Japan

[21] Appl. No.: 633,984

[22] Filed: Dec. 26, 1990

[30] Foreign Application Priority Data

Jan. 5, 1990 [JP] Japan .................................. 2-886
Jun. 20, 1990 [JP] Japan ................................ 2-162362

[51] Int. Cl.⁵ ...................... A61K 37/24; C07K 3/12
[52] U.S. Cl. .................................... 514/12; 514/3; 530/303; 530/399; 530/427
[58] Field of Search ............................ 514/2, 3, 12, 4; 530/303, 399, 305, 427

[56] References Cited

U.S. PATENT DOCUMENTS

| | | | |
|---|---|---|---|
| 4,139,611 | 2/1979 | Wacker et al. | 424/101 |
| 4,371,523 | 2/1983 | Grodsky et al. | 514/3 |
| 4,774,091 | 9/1988 | Yamahira et al. | 424/85.1 |
| 4,816,568 | 3/1989 | Hamilton, Jr. et al. | 530/399 |
| 4,985,404 | 1/1991 | Mitchell | 530/400 |

FOREIGN PATENT DOCUMENTS 0308238  3/1989  European Pat. Off. .

*Primary Examiner*—Jeffrey E. Russel
*Attorney, Agent, or Firm*—Oblon, Spivak, McClelland, Maier & Neustadt

[57] ABSTRACT

The present invention relates to a dried composition containing IGF-I which is highly soluble and has a long shelf life stability. The present invention further relates to a method of preparing a dried composition containing IGF-I by drying a solution containing IGF-I together with a strong acid which is hydrochloric acid, hydrobromic acid, nitric acid, methanesulfonic acid, sulfuric acid, phosphoric acid, or oxalic acid.

4 Claims, No Drawings

METHOD FOR PREPARING A DRIED COMPOSITION OF INSULIN-LIKE GROWTH FACTOR I

FIELD OF THE INVENTION

This invention relates to a method for preparing a dried composition containing insulin-like growth factor I (hereinafter referred to as IGF-I).

BACKGROUND OF THE INVENTION

IGF-I is an insulin-like peptide occurring in the blood and having activity to promote proliferation of various cells, and the production and secretion thereof are dependent on growth hormone.

While IGF-I is a substance in the somatomedin series which mediate the bone growth-promoting effect of growth hormone, it is particularly dependent on growth hormone and, being identified with somatomedin C, it is markedly associated with manifestation of the effect of growth hormone.

Recently, IGF-I has been made available with comparative ease by genetic engineering technology and is known to find application as a therapeutic agent for pituitary dwarfism and a growth promoter for low-height individuals by taking advantage of its growth-promoting activity, as a prophylactic and therapeutic agent for osteoporosis and a therapeutic agent for bone fracture by taking advantage of its chondrocyte proliferating action, as a therapeutic agent for diabetes by taking advantage of its insulin-like activity, and as a therapeutic agent for ulcers, traumas and burns by taking advantage of its protein anabolic action.

However, being a polypeptide of high molecular weight, a dried preparation of IGF-I forms gels on reconstitution to give a non-homogenous solution or undergoes change to a different substance on aging as the result of partial oxidation or deamidation of its polypeptide.

Under the circumstances the inventor of the present invention assiduously attempted to develop a method for preparing a dried composition containing IGF-I which would be highly soluble and have a long shelf-life. As a consequence, the inventor found that a method for preparing a dried composition which comprises drying a solution containing IGF-I together with a strong acid selected from the group consisting of hydrochloric acid, hydrobromic acid, nitric acid, methanesulfonic acid, sulfuric acid, phosphoric acid and oxalic acid is highly soluble and insures long-term stability. This finding and subsequent research led the inventor to the present invention.

DETAILED DESCRIPTION OF THE INVENTION

In this invention, the method for preparing the dried composition containing IGF-I comprises drying a solution containing IGF-I and a strong acid.

IGF-I as it is employed in this invention includes various species of IGF-I derived from mammals such as human being, cattle, etc. by any of recombinant DNA technology (see U.S. Ser. No. 217,885, filed Jul. 11, 1988 now U.S. Pat. No. 5,019,500), peptide synthesis, cell culture, etc., as well as muteins which have IGF-I activity and are obtainable by partial modification of amino acid sequence of IGF-I using conventional recombinant DNA technology(insertion, substitution, addition or deletion of amino acids.

The aforesaid strong acid is selected from hydrochloric acid, hydrobromic acid, methanesulfonic acid, sulfuric acid, nitric acid, phosphoric acid and oxalic acid.

The preferred proportion of said strong acid per milligram of IGF-I in said solution containing IGF-I and strong acid is about 0.5 $\mu$mol to about 10 $\mu$mol and preferably about 1 $\mu$mol to about 5 $\mu$mol in the case of hydrochloric acid, hydrobromic acid or nitric acid, about 1 $\mu$mol in the case of methanesulfonic acid or phosphoric acid, and about 0.5 $\mu$mol in the case of sulfuric acid or oxalic acid.

The method of drying may be lyophilization (freeze-drying), drying under reduced pressure or the like, which can be carried out in a conventional manner. In the resulting dried composition containing IGF-I, there may be incorporated an excipient such as proteins (e.g. water-soluble gelatin, human serum albumin, etc.), neutral high polymers (e.g. dextran etc.), saccharides (e.g. sorbitol, mannitol, etc.), amino acids (e.g. tryptophan, lysine, glutamic acid, etc.), and salts (e.g. sodium chloride etc.), as well as other medicaments such as insulin, growth hormone and so on.

The dried composition of this invention is quite satisfactory in both solubility and shelf-life.

The following examples are further illustrative of this invention.

EXAMPLES

The following solutions 1 through 9 were respectively put into 10 ml vials and, after through mixing, lyophilized. The vials were then sealed with rubber stoppers and caps to give vials 1 through 9 containing lyophilized samples corresponding to the solutions 1 through 9, respectively.

| | | |
|---|---|---|
| (Solution 1) | 0.001N hydrochloric acid containing IGF-I (1 mg) | 1.0 ml |
| (Solution 2) | 0.005N hydrochloric acid containing IGF-I (1 mg) | 1.0 ml |
| (Solution 3) | 0.001N hydrobromic acid containing IGF-I (1 mg) | 1.0 ml |
| (Solution 4) | 0.001N nitric acid containing IGF-I (1 mg) | 1.0 ml |
| (Solution 5) | 0.001N methanesulfonic acid containing IGF-I (1 mg) | 1.0 ml |
| (Solution 6) | 0.001N sulfuric acid containing IGF-I (1 mg) | 1.0 ml |
| (Solution 7) | 0.001M phosphoric acid containing IGF-I (1 mg) | 1.0 ml |
| (Solution 8) | An aqueous solution containing 0.001N oxalic acid and IGF-I (1 mg) | 1.0 ml |
| (Solution 9) (Control) | An aqueous solution containing 0.01% acetic acid and IGF-I (1 mg) | 1.0 ml |

The above pharmaceutical compositions in vials were stored at 50° C. for 1 month and the clarity of the solutions and the residual amounts of IGF-I were determined, respectively.

With regard to the clarity of solutions, 2 ml of distilled water was added to each lyophilizate and the clarity of the solution was visually examined.

For determination of the residue amount of IGF-I, 2 ml of distilled water and 10 $\mu$l of 1N-hydrochloric acid were added to each lyophilizate for complete dissolution and the resulting homogenous solution was analyzed by ion exchange chromatography under the following conditions.

HPLC conditions

| | |
|---|---|
| Column | TSK-GEL CM-2SW 5 μm (Tosoh Corporation) 25 cm × 4.6 mm φ |
| Mobile phase | 0.01 M NaCl 0.05 M Sodium phosphate buffer (pH 6.5) |
| Injection volume | 10 μl |
| Wavelength | 214 nm |

Stability test of the preparations
(stored at 50° C. for one month)

| Preparation in vial | Clarity | % Residue remained |
|---|---|---|
| 1 | Clear | 97.3% |
| 2 | Clear | 91.5% |
| 3 | Clear | 95.0% |
| 4 | Clear | 95.5% |
| 5 | Clear | 98.0% |
| 6 | Clear | 96.5% |
| 7 | Clear | 97.0% |
| 8 | Clear | 86.3% |
| 9 (Control) | Insoluble materials | 52.5% |

It is apparent from the above results that the compositions containing IGF-I which were prepared by using the method of this invention are excellent in both solubility and stability.

What is claimed is:

1. A method for preparing a dried composition comprising insulin-like growth factor I which comprises drying a solution comprising insulin-like growth factor I together with a strong acid selected from the group consisting of hydrochloric acid, hydrobromic acid, nitric acid, methanesulfonic acid, sulfuric acid, phosphoric acid and oxalic acid.

2. The method of claim 1 wherein said strong acid is hydrochloric acid.

3. A dried composition which is prepared by the method of claim 1.

4. The dried composition which is prepared by the method of claim 2

* * * * *